US005667787A

United States Patent [19]
Jackson et al.

[11] Patent Number: 5,667,787
[45] Date of Patent: Sep. 16, 1997

[54] PURIFICATION OF A PERTUSSIS OUTER MEMBRANE PROTEIN

[75] Inventors: Gail Jackson, Richmond Hill; Raafat Fahim; Larry Tan, both of Mississauga; Pele Chong, Thornhill; John Vose, Aurora; Michel Klein, Willowdale, all of Canada

[73] Assignee: Connaught Laboratories Limited, North York, Canada

[21] Appl. No.: 433,644

[22] Filed: May 4, 1995

Related U.S. Application Data

[63] Continuation of Ser. No. 930,595, filed as PCT/CA91/00110, Mar. 4, 1991, Pat. No. 5,444,159.

[30] Foreign Application Priority Data

Apr. 4, 1990 [GB] United Kingdom ............... 9007657

[51] Int. Cl.$^6$ ............... A61K 39/10; A23J 1/00; C08H 1/00; C07K 1/00
[52] U.S. Cl. ............... 424/253.1; 424/254.1; 530/412; 530/414; 530/416; 530/417; 530/418
[58] Field of Search ............... 424/254.1; 530/412, 530/414, 416, 417, 418, 825

[56] References Cited

U.S. PATENT DOCUMENTS

| | | | |
|---|---|---|---|
| 4,997,915 | 3/1991 | Tan et al. | 530/396 |
| 5,101,014 | 3/1992 | Burns et al. | 530/350 |
| 5,237,052 | 8/1993 | Novotny | 530/350 |
| 5,276,142 | 1/1994 | Gotto | 530/413 |

FOREIGN PATENT DOCUMENTS

| | | |
|---|---|---|
| 0162639 | 11/1985 | European Pat. Off. |
| 0336736 | 10/1989 | European Pat. Off. |

OTHER PUBLICATIONS

Brennan, M.J. et al., *Infect. Immun.* 56: 3189–3195, 1988.
Brennan, M.J. et al., *Tokai J. Exp Clin Med.*, 15:211–215, 1988.
Novotny, P. et al., *Infect. Immun.*, 50: 199–206, 1985.
Novotny, P. et al., *Develop. biol. Standard*, 61: 27–41, 1985.
Sato, Y. et al., *The Lancet*, Jan. 21, 1984, pp. 122–126.
Betsou, F. et al., *Infect. Immun.* 63: 3309–3315, 1995.
Confer, D.L., Eaton, J.W., *Science*, vol. 217: 948–950, 1982.
Guiso, N. et al., Sixth International Pertussis Symposium, pp. 207–211.
Monneron, A. et al, *Biochemistry* 1988, 27: 536–539.
Greco, D. et al., *N. Engl. J. Med.* 334(6): 341–348, Feb. 8, 1996.
Gustafsson, L. et al., *N. Engl. J. Med.* 334(6): 349–355, Feb. 8, 1996.
Westcott et al. 1979, *Proc. Natl. Acad. Sci. USA* 76: 204–208.
Hewlett and Gordon, 1988, pp. 193–209, Pathogenesis and Immunity in Pertussis (Eds Wardlaw and Parton) John Wiley and Sons, Ltd.
Gould-Kostka et al. 1990, *FEMS Microbiol. Lett.* 67: 285–290.

BioRad Bulletin 1107 "AffiGel Blue Affinity Chromatography Gel for Enzyme and Blood Protein Purification".
Betsou et al. 1995, *Gene.* 162: 165–166.
Cronin et al. 1986, *Amer. J. Physiol.* 251: E164–171.
Hewlett 1984, *Ann. Intern. Med.* 101: 653–666.
Ladant et al. 1986, *J. Biol. Chem.* 261: 16264–16269.
Wolff et al. 1986, *Biochemistry* 125: 7950–7955.
Weiss et al. 1983. *Infect. & Immun.* 42(1): 33–41.
Charles et al., 1988, Tokai J. Exp. Clin. Med., vol. 13, Suppl pp. 227–234.
Airaksinen et al., 1991, Biotechnology Letters vol. 13, No. 5, 305–310.
Brennan et al., Abstract 1990.
Gould–Kosta et al., 1989 Abstract B–126.
Brennan, M.J. et al., Infection and Immunity, vol. 56, No. 12, Dec. 1988, Washington, pp. 3189–3195, "Identification of a of a 69–Kilodalton Nonfimbrial Protein as an Agglutinogen of Bordettella Pertussis."
Magistris, M.T. et al., The Journal of Experimental Medicine, vol. 168, No. 4, 01 Oct. 1988, New York, pp. 1351–1362, "Dissecting Human T Cell Response Against Bordetella Species."
Hedenskog, S. et al., Pertussis Toxoid Vaccine, AJDC–vol. 141, Aug. 1987.
Storsaeter, J. et al., Vaccine, vol. 8, Oct. 1990.
Montaraz, J.A. et al., Infection and Immunity, Mar. 1985, pp. 744–751.
Halperin, S.A. et al., 30th ICAAC, Atlanta, GA, Official Abstract Form.
Thomas, M.G. et al., The Journal of Infectious Diseases, vol. 159, No. 2, Feb. 1989, pp. 211–218.
Gould–Kostka, J.L. et al., FEMS Microbiology Letters 67 (1990) 285–290.
Shahin et al J. Exp Med 171(1): 63–73, 1990.
Gustagsson et al, N. Engl. J. Med. 334(6): 349–55, Feb. 8, 1996.

(List continued on next page.)

*Primary Examiner*—James C. Housel
*Assistant Examiner*—V. Ryan
*Attorney, Agent, or Firm*—Sim & McBurney

[57] ABSTRACT

Pertactin (formerly 69 kDa protein) is recovered in stable biologically pure form having no detectable adenylate cyclase activity from fermentation broth from the fermentation of Bordetella pertussis as well as from the cells. The broth is processed to selectively remove pertussis toxin (PT) and filamentous haemagglutinin (FHA), the pertactin is precipitated by ammonium sulphate and the precipitate is dissolved in buffer at pH 6.0 to 8.5, the solution then is passed through hydroxyapatite and ion-exchange chromatograph columns before final ultrafiltration. Cells are extracted with urea and the extract ultrafiltered and diafiltered. The pertactin is precipitated from the extract and the precipitate processed as above. In a variation, the broth is contacted with ammonium sulphate to precipitate pertactin, PT and FHA, the precipitate is dissolved and the PT and FHA selectively removed, before the solution is passed to the chromatograph columns.

11 Claims, No Drawings

OTHER PUBLICATIONS

Sato et al. Lancet, pp. 122–126, Jan. 21, 1984.

Brennan et al. Injection and Immunity 56(12): 3189–3195, 1988.

Brennan et al. Tokai J. Exp. Clin Med. 13 Suppl: 211–215, 1988.

Shahin et al. Journal of Experimental Medicine 171:63–73, 1990.

Greco et al. N. Engl. J. Med. 334(6): 341–348, Feb. 8, 1996.

PURIFICATION OF A PERTUSSIS OUTER MEMBRANE PROTEIN

This is a continuation of application Ser. No. 07/930,595, filed as PCT/CA91/00110, Mar. 4, 1991, now U.S. pat. No. 5,444,159.

FIELD OF INVENTION

The present invention relates to a novel process for the purification of an outer membrane protein of Bordetella pertussis, having a molecular weight of approximately 69,000 Daltons, formerly called the 69 kDa protein and now called pertactin, and obtained from the fermentation broth and cellular extracts of the said organism. The protein obtained by the process is to be used in a "component" vaccine to protect against the disease of whooping cough.

BACKGROUND TO THE INVENTION

The disease of whooping cough or pertussis is a result of infection by Bordetella pertussis, and is a serious and debilitating human disease particularly in young children. For the last fifty years the disease has been controlled through large-scale immunization programmes. The current licensed vaccine in North America is a "whole cell" vaccine prepared by growing the organism in fermentors and then treating the resulting B. pertussis cells with chemical agents, such as formaldehyde, to kill the organism and inactivate toxic proteins. The cells are resuspended and then used directly or in combination with other antigens. This vaccine, although highly efficacious, has been associated with clinical symptoms that include fever, local reactions, high-pitched crying and convulsions. Despite the fact that there is no proven relation between these symptoms and the vaccine, there has been decreased public acceptance of this vaccine and in a number of countries, e.g. Japan, Sweden and the U.K., decreased immunization has led to outbreaks of the disease. The need for a more defined vaccine has been recognized and considerable effort has been directed by several manufacturers and researchers towards the development of an efficacious pertussis vaccine that consists of a small number of highly purified proteins. This vaccine has been termed a component vaccine.

This search has been hampered by a lack of information on the mechanism of pathogenesis of B. pertussis. Many virulence associated factors, such as pertussis toxin (PT), also known as lymphocytosis promoting factor (LPF), filamentous haemagglutinin (FHA), adenylate cyclase, lipopolysaccharide, agglutinogens and other outer membrane proteins have been suggested for inclusion in an "acellular" vaccine, which is less defined than the component vaccine. Much of the work on acellular vaccines has concentrated on a PT-based vaccine. Results of a recent clinical trial have indicated that a vaccine consisting entirely of PT-toxoid only partially protected children from the infection. A PT/FHA combination showed slightly higher efficacy but this was still lower than that obtained for the whole-cell vaccine.

One potential protective antigen is an outer membrane protein, with a molecular weight of approximately 69,000 daltons (pertactin) found on all virulent strains of B. pertussis. This protein is produced in relatively large amounts during the culture of the organism and can be purified from either the fermentation broth or from cell extracts. The present invention provides a novel method of effecting such purification.

The potential importance of this outer membrane protein for inclusion in a human vaccine against whooping cough was suggested from attempts to prepare a vaccine to protect pigs against B. bronchiseptica infection. Cell-surface extracts of B. bronchiseptica were used to immunize sows. Levels of antibody to a cell surface antigen with a molecular weight of 68,000 daltons correlated with protection of newborn piglets against infection. Similar antigens, with similar molecular weights, were detected in B. pertussis (approximately 69,000 daltons) and in B. parapertussis (approximately 70,000 daltons). Immunization with the protein obtained from B. pertussis protected mice against intracerebral challenges with live organisms and antibodies to the protein conferred passive protection to mice in this test. Both active and passive protection of mice in an aerosol challenge model have also been described.

The published procedures for purification of pertactin do not allow for the large-scale production of highly purified, non-pyrogenic and stable antigen. One reported method (Canadian Patent No. 1,253,073) involves acid-glycine extraction of the cells, anion-exchange chromatography and preparative iso-electric focussing. However, the pertactin obtained has been reported to degrade into smaller fragments, to be sensitive to low pH and to have adenylate cyclase activity. For these reasons, this extraction procedure is considered undesirable for large-scale production. In addition, iso-electric focussing is not amenable to large-scale production. A second procedure (U.S. Pat. No. 5,101,014) involved the extraction of the outer membrane protein from the cells of an afimbriated strain of B. pertussis. The protein was purified by a combination of DEAE-Sepharose and Affigel-blue chromatographies. The potential of leaching the blue dye into the product would be a possible safety concern. Neither method addresses the purification of pertactin directly from fermentation broths.

SUMMARY OF INVENTION

In one embodiment of the present invention, pertactin is obtained in large quantities from fermentor broth, which is the preferred source, and in a purified form, by using the method described below. The protein can be included in a product to be used for the widespread vaccination of children against whooping cough.

After growing the organism in a fermentor, the cells are removed by centrifugation and filtration and the supernatant reduced in volume and sterilized. The broth is diluted to a low ionic strength and, after removal of other antigens, the pertactin is isolated by chromatography on various substrates and further purified by ultrafiltration. The protein can also be isolated from the cells after extraction with urea, centrifugation and further processing to give a solution that can be treated as described above.

Accordingly, in one aspect, the present invention provides a method for the production of pertactin, which comprises providing an impure aqueous solution of pertactin substantially free from other Bordetella antigens, purifying pertactin in said aqueous solution by passing said aqueous solution sequentially in contact with hydroxyapatite and an ion-exchange, and subjecting the resulting purified solution to ultrafiltration.

The resulting product is very stable when purified by this method and has no detectable adenylate cyclase activity. Accordingly, another aspect of the invention provides a biologically pure and stable pertactin having no detectable adenylate cyclase activity.

GENERAL DESCRIPTION OF INVENTION

The process described in this invention allows for the purification of several protein antigens for possible inclusion in a component pertussis vaccine from a single fermentation of B. pertussis.

In the present invention, B. pertussis is grown in a fermentor under controlled conditions. Carbon sources and growth factors are supplemented either continuously or in batches at various intervals during the fermentation until the pertussis proteins (PT, FHA and pertactin) are at the desired levels as determined by a specific enzyme-linked immunosorbent assay (ELISA) for each antigen. The fermentor broth is harvested, the majority of the cells removed by centrifugation and the broth sterilized by microfiltration, preferably using known membrane filters of about 0.2 micron pore size. The broth is concentrated, say 10-fold, by membrane ultrafiltration and used for the purification of pertussis toxin and FHA (see published European Patent Application No. 0,336,736; U.S. Pat. No. 4,997,915, the disclosure of which is incorporated herein by reference). The cells are the source of material for the purification of the agglutinogens. Pertactin can be purified from both the broth or cells. The former is preferred as the majority of the protein is found in the broth.

The first stage in the purification of the pertactin requires dilution of the broth to a low ionic strength and chromatography on Perlite or other suitable solid particulate adsorbent material to remove the PT and FHA antigens, as more fully described in the aforementioned published European Patent Application No. 0,336,736, U.S. Pat. No. 4,997,915). The PT and FHA antigens can be removed from the adsorbent material by treatment with an aqueous medium of high ionic strength for use in a component pertussis vaccine.

As used herein, the term "low ionic strength" refers to an aqueous medium having a conductivity of about 11 mS/cm or less, preferably about 4 mS/cm or less. The unit of measurement mS/cm is millisiemen per centimeter. A Siemen (S) is a unit of conductivity and is the equivalent of the inverse of resistance (ohm) and is sometimes designated mho. The term "high ionic strength" as used herein refers to an aqueous medium having a conductivity of greater than about 11 mS/cm and preferably at least about 50 mS/cm.

The remaining mixture then is concentrated by membrane filtration, subjected to ammonium sulphate precipitation and the resulting pellet dissolved in low ionic strength buffer, such as Tris-.HCl, at a pH of 6.0 to 8.5 to yield a solution with a final conductivity of generally less than about 4 mS/cm, typically approximately 3.4 mS/cm. The solution is chromatographed sequentially on hydroxyapatite, and an ion exchange medium, such as Q-Sepharose®. Pertactin elutes in the unbound fraction of both columns under the specified buffer conductivity. However, if the conductivity is lower than 1.5 mS/cm for hydroxyapatite or 2.8 mS/cm for Q-Sepharose®, pertactin binds to both columns and can be eluted with a buffer having conductivities 1.5 mS/cm or greater for hydroxyapatite and 2.8 mS/cm for or greater Q sepharose.

The pertactin is further purified by ultrafiltration through about 100 to 300 kDa Nominal Molecular Weight Limit (NMWL) membranes where it is collected in the filtrate, concentrated using membranes with a NMWL of about 30 kDa or less and sterile filtered for use in combination with other pertussis antigens in a vaccine.

In an alternative procedure, pertactin along with FHA and PT are precipitated from fermentor broth, by addition of ammonium sulphate. The precipitate is removed from the residual broth and redissolved to provide an aqueous solution suitable for processing as described above first to remove the PT and FHA and then to purify the pertactin.

Pertactin also can be purified from B. pertussis cells. The cells are extracted in a solution containing a high concentration (for example, 4M) of urea for, say 1.5 hr. at room temperature. Cell debris is removed by centrifugation and the supernatant, which contains the protein, is subjected to ultra-filtration using 100 to 1000 kDa NMWL membranes. High molecular weight proteins, such as the agglutinogens, are retained while the majority of the pertactin is filtered through. The filtrate is concentrated, diafiltered using a 30 kDa or less NMWL membrane, and then precipitated by ammonium sulphate and centrifuged to give a pellet for processing as described above.

Pertactin, although reportedly susceptible to proteolytic cleavage, is very stable when purified by the method of the invention. SDS-PAGE analysis indicates that the purified pertactin is homogenous and essentially intact with traces of degradation products of molecular weights between 30 and 40 kDa. No evidence for further degradation or change in immunogenicity was found after several months of storage at 2° to 8° C. or at higher temperatures (24° C., 37° C.). In contrast to a previous publication (Canadian Patent No. 1,253,073), the finding that the pertactin prepared by this method does not show any detectable adenylate cyclase activity and has enhanced stability makes it an ideal candidate for inclusion into a component vaccine for protection against B. pertussis.

EXAMPLES

Methods of protein biochemistry, immunochemistry used but not explicitly described in this disclosure and these Examples, are amply reported in the scientific literature and are well within the ability of those skilled in the art.

Example 1

This Example illustrates the growth of B. pertussis in fermentors.

B. pertussiswas seeded into a fermentor containing 250L of broth (modified Stainer-Scholte medium). During the period of fermentation, monosodium glutamate and the growth factors, glutathione, ferrous sulphate, calcium chloride, ascorbic acid, niacin and cysteine were added during the fermentation process to increase antigen yields. At the end of a 48 hr. fermentation period, the broth was centrifuged to remove the majority of cells and the supernatant, which contains PT, FHA and most of the pertactin, was further clarified by ultrafiltration through cellulose acetate membranes (0.22μm pore size). The sterilized filtrate was concentrated approximately 10-fold using a 20 kDa NMWL membrane and assayed for protein content and for antigen by antigen-specific ELISAs.

Example 2

This Example illustrates the large-scale removal of PT and FHA using a chromatographic column of Perlite.

The broth concentrate, prepared as described in Example 1, was diluted with water to a conductivity of ≦14 mS/cm and subjected to chromatography on a Perlite column (12 cm[H]×37 cm[D]), previously equilibrated with water, at a protein to Perlite ratio of approximately 3 mg per milliliter and a linear flow rate of approximately 100 cm/hr. Proteins bound to the Perlite were almost exclusively PT and FHA while pertactin was found in the flow-through.

Example 3

This Example illustrates the precipitation of pertactin using ammonium sulphate fractionation.

The flow-through fraction from Example 2 was concentrated to a volume of approximately 10 liters by ultrafiltration using 10 kDa NMWL membranes. The resultant solution usually had a protein concentration of 1 to 2 mg/ml. While stirring at room temperature, ammonium sulphate (3.5 Kg/10L of concentrate or 35% w/v) was slowly added, and the mixture left to dissolve before transferring to a refrigerator at 2° to 8° C. and stirred for an additional two hours, preferably overnight. The precipitate was collected by centrifugation and dissolved in 2 liters of 10 mMTris.HCl, pH 6.0 to 8.5. A second ammonium sulphate fractionation (25% w/v) was effected by slowly adding ammonium sulphate (500 g) to the 2 liters of solution and stirring for at least 2 hours after the solution was cooled to 2° to 8° C., usually overnight. Finally the precipitate was collected by centrifugation, dissolved in 2L of Tris.HCl, pH 7.5, and the conductivity adjusted to approximately 3.4 mS/cm by adding either ammonium sulphate (if below 3.4 mS/cm) or 10 mM Tris.HCl, pH 7.5 (if higher than 3.4 mS/cm).

Example 4

This Example illustrates the precipitation of pertactin from pertussis fermentation broth concentrates.

Ammonium sulphate (250 g/L of broth) was added to fermentor broth concentrates and the mixture stirred for more than two hours after the mixture had reached 2° to 8° C. The precipitate was collected by centrifugation, dissolved in 10 mM Tris.HCl, pH 7.5, and the same buffer added until the conductivity was ≦4.0 mS/cm. This solution contained all the PT, FHA and pertactin. The solution was subjected to Perlite chromatography (as described in Example 2) to remove PT and FHA and the Perlite flow-through was subjected to hydroxyapatite and Q-Sepharose® chromatography (see Example 5).

Example 5

This Example illustrates the chromatography of pertactin on hydroxyapatite and Q-Sepharose®.

Hydroxyapatite was packed into a suitable size column, preferably 5 cm [D]×10 cm [H] and equilibrated with 10 mM Tris.HCl, buffer, pH 7.5, containing 15 mM ammonium sulphate (conductivity approximately 3.4 mS/cm). Q-Sepharose® was packed into a similar column and equilibrated with the same buffer. The two columns were connected in series with the hydroxyapatite column upstream of the Q-Sepharose® column. The resolubilized pertactin (from Example 3) when subjected to chromatography on the two columns in series did not bind to the matrices and the flow-through fraction was collected. After filtration through a 300 kDa NMWL membrane, the filtrate containing the pertactin was concentrated and diafiltered using ≦130 kDaNMWL membranes and finally sterile filtered using a 0.22μm membrane.

Example 6

This Example illustrates the purification of pertactin by binding to Q-Sepharose®.

The Perlite flow-through fraction from Example 2, was concentrated to approximately 7L, having a protein concentration usually between 1.5 to 3.0 mg/ml. Solid ammonium sulphate was added to the concentrate at a ratio of approximately 35% (w/v). The mixture was stirred for 2 or more hours at 2° to 8° C. The collected precipitate was dissolved in approximately 500 ml of 10 mM Tris.HCl, pH 8.0, and then precipitated with ammonium sulphate (100 g/L). After a minimum of 2 hr. stirring at 2° to 8° C., the supernatant was isolated by centrifugation. An additional aliquot of ammonium sulphate (100 g/L) was added to the supernatant to precipitate the pertactin. The precipitate was dissolved and adjusted with 10 mM Tris.HCl, pH8.0, to a conductivity of approximately 3.4 mS/cm. The pertactin is purified according to Example 5 by passing through tandem hydroxyapatite/Q-Sepharose® columns (each 11 cm [D]×8 cm [H]), ultrafiltered through a 300 kDa membrane and concentrated with a 10 to 30 kDa membrane. The pertactin then was solvent-exchanged by either dialysis, diafiltration or using a solvent exchange column into a solution in 10 mM Tris.HCl, pH 8.0 (conductivity approximately 0.6 mS/cm), then bound to a Q-Sepharose® column (11 cm [D]×8 cm [H]) equilibrated in.10 mMTris.HCl, pH 8.0. The column was washed with 10 mM Tris.HCl, pH 8.0, containing 5 mM ammonium sulphate (conductivity approximately 1.7 mS/cm) and the pertactin was eluted with 10 to 100 mM (preferably 50 mM) phosphate buffer at pH 8.0. The purified pertactin is solvent exchanged into PBS and sterile filtered.

Alternatively, after the ammonium sulphate precipitation steps, the pertactin solution with an ionic strength adjusted to approximately 3.4 mS/cm is passed through the hydroxyapatite column alone. The run-through fraction is concentrated and solvent exchanged into 10 mM Tris.HCl, pH 8.0 and bound directly onto the Q-Sepharose® column. After washing with 10 mM Tris.HCl, pH 8.0, containing 5 mM ammonium sulphate, the pertactin is eluted from the Q-Sepharose® column with 10–100 mM (preferably 50 mM) phosphate buffer at pH 8.0. The purified pertactin is ultrafiltered through a 300 kDa membrane, concentrated and diafiltered with a 10 to 30 kDa membrane and sterile filtered.

Example 7

This Example illustrates the extraction of pertactin from B. pertussis cells.

B. pertussis cells (5% w/v) were suspended in phosphate buffered saline (10 mM sodium phosphate, pH 7.5, 0.15M sodium chloride {PBS}) containing 4M urea and the suspension was dispersed for 15 seconds to 60 minutes, and stirred for 1.5 hr. at room temperature. Cell debris was removed by centrifugation at 5 to 6,000×g. The cellular extract was filtered through 100 kDa or 300 kDa membranes and the retentate diafiltered with 2 to 3 volumes of PBS. The filtrate from the membranes and the diafiltrate were combined and concentrated to one-fifth the original volume using ≦+ kDaN WML membranes and further diafiltered With 5 volumes of PBS.

Example 8

This Example illustrates the preparation of pertactin from extracts of *B. pertussis* cells.

The retentate from Example 7 was precipitated by the slow addition of ammonium sulphate (25% w/v) at room temperature and the mixture allowed to stir at 2° to 8° C. for an additional 2 hrs, preferably overnight. The precipitate was dissolved in 10 mM Tris.HCl buffer, pH 7.5, and saturated ammonium sulphate solution added to achieve a conductivity corresponding to that of 10 mM Tris.HCl, pH 7.5, containing 15mM ammonium sulphate (3.5 mS/cm). The pertactin was then in a form for purification by hydroxyapatite/Q-Sepharose® chromatography as described in Example 5.

Example 9

This Example illustrates the immunogenicity of pertactin combined with other antigens.

A solution of purified pertactin was mixed with aluminum phosphate (3 mg/ml) and varying amounts of pertactin (1 to 20 μg) were combined with constant amounts of PT toxoid, FHA toxoid and agglutinogens. Guinea pigs (10 per group and with a 400 to 450 g weight range) were injected at days 0 and 21 and were bled at day 28. A good antibody response to pertactin was observed with doses as low as 1 μg. No significant difference in antibody responses was observed between doses of 1 to 10 µg and consistency was obtained between various lots of pertactin (See Table I below).

Example 10

This Example illustrates the stability of purified pertactin.

The stability of the pertactin antigen was monitored with and without combination with aluminum phosphate and after combination with other pertussis antigens in a candidate vaccine formulation. Samples of pertactin (without aluminum phosphate) were stored for various times at −20° C., 2° to 8° C., 24° C. and 37° C. Two lots were studied with different preservatives (thimerosal and phenoxy-ethanol). It was noticeable that whichever preservative was used there was no reduction in the pertactin-specific ELISA value up to 3 months. A reduction was observed with phenoxyethanol as a preservative in the 6 and 12 month values. The results are reproduced shown in Table II below.

Potential vaccine combinations in aluminum phosphate were stored at 2° to 8° C., 24° C. and 37° C. Stability of the antigen was monitored by general appearance, pertactin-specific ELISA, protein content, SDS-PAGE, Western blot analysis with monospecific anti-pertactin antisera and immunogenicity studies in guinea pigs. The pertactin has shown no changes in stability for any storage time whether alone or in combination with either adjuvant or other antigens, as shown in Table III below. The materials used for the experiment were pertactin alone with aluminum phosphate adjuvant and vaccine combinations with aluminum phosphate.

SUMMARY OF DISCLOSURE

In summary of this disclosure, the present invention provides novel procedures for recovery of pertactin in stable form suitable for incorporation as a component in a component vaccine, from fermentation products of Bordetella species, using column chromatography and ultrafiltration. Modifications are possible within the scope of this invention.

TABLE I

DOSE RESPONSE AND CONSISTENCY OF PRODUCTION OF PERTACTIN

| LOT # | ANTIGEN µG | 69 kDa SPECIFIC ELISA µg/ml | ANTI-69 kDa TITRES[a] |
|---|---|---|---|
| 69 kDa | 2.0 | — | 9.90 ± 0.8 |
| 69 kDa | 20.0 | — | 10.80 ± 0.7 |
| CP4DT001* | 6.0 | 5.40 | 9.00 ± 1.20 |
| CP4DT003A* | 6.0 | 6.57 | 9.00 ± 0.58 |
| CP4DT004A* | 6.0 | 6.53 | 9.00 ± 1.07 |

[a]= $Log_2$(reactive titres/100): eight animals/group
*= These materials were vaccine preparations.
Dose: The antigens were dissolved in 1 ml and the dose/animal was 0.5 ml on Day 0 and 0.5 ml on Day 21. Animals were bled on Day 28

TABLE II

STABILITY OF UNADSORBED PERTACTIN

| SAMPLE | TIME MONTHS | STORAGE TEMP (°C.) | PROTEIN[a] µG/ML | ELISA µG/ML |
|---|---|---|---|---|
| G2361-TH | 0 | — | 149[b] | ND |
| | 1 | 6 | 125 | 143 |
| | | 24 | 140 | 173 |
| | | 37 | 136 | 131 |
| | 2 | 6 | 117 | 169 |
| | | 24 | 120 | 163 |
| | | 37 | 119 | 127 |
| | 3 | 6 | 132 | 156 |
| | | 24 | 153 | 134 |
| | | 37 | 128 | 103 |
| | | −20 | 149 | 160 |
| | 6 | 6 | 117 | 130 |
| | | −20 | 126 | 104 |
| | 12 | 6 | 126 | 151 |
| | | −20 | 119 | 131 |
| G2361-P | 0 | — | 149[b] | ND |
| | 1 | 6 | 114 | 127 |
| | | 24 | 129 | 128 |
| | | 37 | 125 | 124 |
| | 2 | 6 | 125 | 121 |
| | | 24 | 116 | 128 |
| | | 37 | 132 | 124 |
| | 3 | 6 | 189 | 126 |
| | | 24 | 119 | 128 |
| | | 37 | 147 | 78 |
| | 6 | 6 | 103 | 94 |
| | 12 | 6 | 117 | 75 |

G2361-TH = Pertactin preparation that contains 0.01% thimerosal as the preservative
G2361-P = Pertactin preparation that contains 0.5% 2-phenoxyethanol as the preservative
[a]= Protein contents of the samples were determined by BCA assay (Pierce) after TCA precipitation of the sample
[b]= Protein content of sample at zero time was determined by Kjeldahl

TABLE III

STABILITY OF PERTACTIN IN VACCINE COMBINATIONS

| LOT # | TIME MONTHS | STORAGE TEMP. (°C.) | ELISA µG/ML | ANTI-69 kDa TITRES[a] |
|---|---|---|---|---|
| A69K001P[b] | 0 | 6 | ND | ND |
| | 3 | 6 | 56 | 10.7 ± 1.28 |
| | 6 | 6 | 42 | 9.9 ± 0.83 |
| A69K002P[c] | 0 | 6 | 99 | 11.2 ± 1.28 |
| | 6 | 6 | ND | 9.9 ± 1.0 |
| A69K003P[d] | 0 | 6 | 58 | 10.9 ± 0.64 |
| | 6 | 6 | ND | 9.5 ± 1.0 |
| CPDT4P[e] | 0 | 6 | 9.44 | 10.1 ± 0.74 |
| | 3 | 6 | 9.63 | 9.0 ± 0.00 |
| | | 24 | 8.43 | 9.0 ± 0.89 |
| | | 37 | 7.35 | 9.2 ± 0.84 |
| | 9 | 6 | 8.19 | 10.5 ± 0.85 |
| | 12 | 6 | 6.72 | 7.5 ± 0.93 |
| CP4DT00[f] | 0 | 5 | 5.4 | 9.0 ± 1.20 |
| | 3 | 5 | 6.55 | 10.6 ± 0.92 |
| | 6 | 5 | 5.67 | 9.1 ± 1.13 |

Note:
For samples b, c and d the sample was diluted to 6 µg/ml of pertactin prior to injection and the animals were given 0.5 ml on Day 0 and 0.5 ml on Day 28.
Note:
For samples e and f the antigens were in 1 ml and the dose was 0.5 ml on Day 0 and 0.5 ml on Day 28
[a]= $Log_2$(reactive titres/100): eight animals/group
[b]= Pertactin solution alone adsorbed with aluminium phosphate. Contained 54 µg/ml of pertactin
[c]= Pertactin solution alone adsorbed with aluminium phosphate. Contained 134 µg/ml of pertactin.
[d]= Pertactin solution alone adsorbed with aluminium phosphate. Contained 77 µg/ml of pertactin.
[e]= Vaccine combination containing 10 µg/ml of pertactin.
[f]= Vaccine combination containing 6 µg/ml of pertactin.

We claim:

1. A component vaccine against disease caused by infection by Bordetella pertussis, which comprises immunoprotective, purified pertactin having no detectable adenylate cyclase activity, as an active component thereof, and a physiologically-acceptable carrier therefor.

2. The vaccine claimed in claim 1, wherein at least one other purified immunoprotective pertussis antigen is present in said vaccine.

3. The vaccine claimed in claim 2, wherein said at least one other purified immunoprotective pertussis antigen is selected from the group consisting of purified pertussis toxin (PT), purified filamentous haemagglutinin (FHA) and purified agglutinogens.

4. Immunoprotective purified pertactin having no detectable adenylate cyclase activity.

5. The pertactin of claim 4 which is isolated and purified from a culture of B. pertussis.

6. The pertactin of claim 4 having no detectable pertussis toxin (PT) activity.

7. The pertactin of claim 4 having no contamination by dye chromatography derived material.

8. A method of immunizing a human host against disease caused by Bordetella pertussis, comprising administering to the host a component vaccine comprising, as a component thereof, purified pertactin devoid of adenylate cyclase activity.

9. The method of claim 8 wherein the vaccine further comprises, as at least one additional component thereof, at least one other purified antigen of Bordetella pertussis selected from the group consisting of purified pertussis toxin (PT), purified filamentous haemagglutinin (FHA) and purified agglutinogens.

10. A component vaccine against disease caused by infection by Bordetella pertussis, which comprises:

as a first component, purified pertactin having no detectable adenylate cyclase activity, as an additional component, at least one other purified *B. pertussis* antigen selected from the group consisting of pertussis toxin (PT), filamentous haemagglutinin (FHA) and agglutinogens; and a pharmacologically acceptable carrier therefor.

11. The component vaccine of claim 10 wherein said pertactin is devoid of contamination by dye chromatography derived material.

* * * * *